United States Patent [19]
Nordstrom et al.

[11] Patent Number: 6,033,388
[45] Date of Patent: Mar. 7, 2000

[54] CATHETER INTRODUCER WITH THIN WALLED SHEATH

[75] Inventors: Jon W. Nordstrom, Winchendon; James P. Culhane, Westboro, both of Mass.

[73] Assignee: Medtronic AVE, Inc., Santa Rosa, Calif.

[21] Appl. No.: 09/058,750

[22] Filed: Apr. 10, 1998

[51] Int. Cl.⁷ .......................... A61M 5/00; A61M 25/00
[52] U.S. Cl. ................................. 604/264; 604/280
[58] Field of Search ...................... 604/264, 280

[56] References Cited

U.S. PATENT DOCUMENTS 4,976,720  12/1990  Machold et al. .
5,069,674  12/1991  Fearnot et al. .
5,702,413  12/1997  Lafontaine .
5,743,876   4/1998  Swanson .

Primary Examiner—Corrine McDermott
Assistant Examiner—Jennifer R. Sadola
Attorney, Agent, or Firm—Sterne, Kessler, Goldstein & Fox PLLC

[57] ABSTRACT

A catheter introducer sheath comprises a polyimide tube manufactured by a dispersion coating process. The inner diameter of the tube is constant over its entire length. The thickness of the tube is 0.005 inches which is an optimal compromise between the size or outer diameter of the sheath and its ability to resist kinking when inserted into the patient's vasculature.

3 Claims, 2 Drawing Sheets

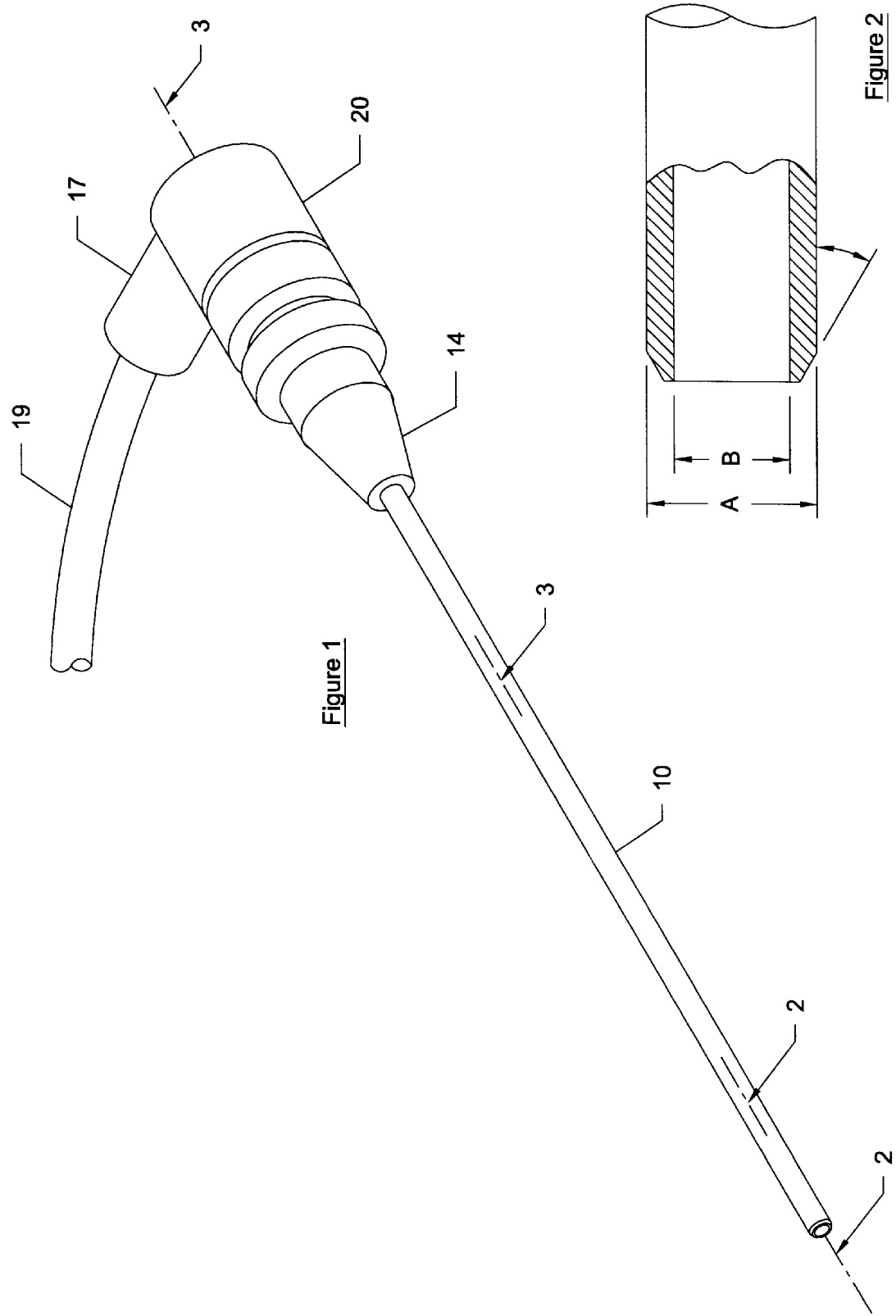

CATHETER INTRODUCER WITH THIN WALLED SHEATH

BACKGROUND OF THE INVENTION

This invention relates to catheter introducers, i.e. to a device which enables the introduction of a catheter, guide wire or the like into a patient's vasculature.

Catheter introducers are used to assist in the introduction of catheters or guide wires into a patient's vascular system (typically an artery) for many different types of intravascular procedures. The introducer (and its associated dilator) must penetrate the skin and wall of the blood vessel and be positioned within the blood vessel so that catheters can be advanced and withdrawn through the introducer. In this way even when multiple catheters or guide wires are required, injury to the patient is limited to the single placement of the introducer through the skin and vessel wall.

For a number of reasons, it is desirable to minimize the outer diameter or profile of an introducer sheath. For one, obstruction of blood flow in the blood vessel is reduced. This is an important consideration in pediatric procedures and when it is necessary to introduce catheters through the arm. Also, a smaller outer diameter reduces the trauma suffered by the patient, and, consequently, the patient's recovery time.

It has been recognized that a thin walled sheath is beneficial. One such introducer sheath known as a Desilets-Hofmann arterial sheath comprised a very thin wall (0.003 inches) which was made by spiral wrapping Mylar™ polyester tape on a mandrel to insure good diameter tolerances and roundness. The edges of the tape are overlapped and bonded with adhesive to yield a cylindrical tube. The tube was then spray coated with a thermoset polyurethane and the tip ground to provide an external taper. The product is no longer on the market.

Currently available catheter introducer sheaths are made from tubing which is manufactured by extrusion. Extrusion is a low cost manufacturing process but results in tubing having a relatively high variation in inner diameter and roundness. Since the introducer sheath must be able to accommodate the outer diameter of the catheter which is to be introduced, a relatively large inner diameter must be specified for an extruded introducer sheath. Accordingly, in the manufacture of known catheter introducers, the extruded tube is heat treated to bring the inner diameter of its distal tip to the more precise values required for a specified catheter. In this way, at least the diameter of the distal tip is minimized.

Another factor which affects the outer diameter or profile of an introducer sheath is the thickness of the wall of the sheath. Conventionally, introducer sheaths are made of polytetrafluoroethylene (PTFE), polyethylenebutylacrylate (PEBA), and polyethelene. The introducer sheath must be stiff enough that it will not kink when it is pushed through the skin and into the blood vessel with the assistance of a dilator. For such materials, typical wall thickness ranges from 0.007 inches to 0.010 inches.

OBJECTS OF THE INVENTION

The principal object of the invention is to provide a cathetheter introducer sheath which, for a given catheter, has a smaller outer diameter than is possible with known prior art catheter introducers.

SUMMARY OF THE INVENTION

In accordance with the invention, a catheter introducer is made from a polyimide tubing material which has been produced by a dispersion process rather than by extrusion. The inner diameter of the introducer is constant over its entire length and the thickness of the tubing is no greater than 0.005 inches. The outer diameter of the distal portion of the introducer sheath is tapered to facilitate penetration of the skin and blood vessel.

IN THE DRAWINGS

FIG. 1 is a perspective view showing a catheter introducer in accordance with the preferred embodiment of the invention;

FIG. 2 is a partial sectional view along the line 2—2 of FIG. 1; and

DETAILED DESCRIPTION

Figure 3:
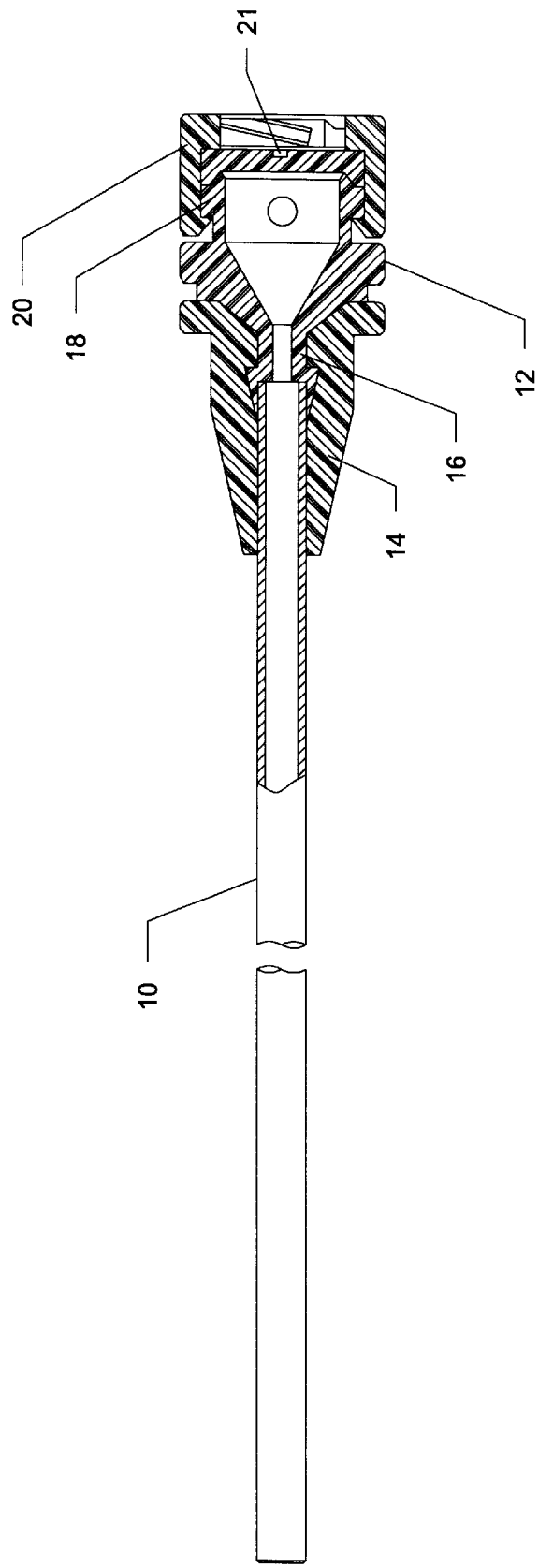
FIG. 3 is a partial longitudinal sectional view along the line 3—3 of FIG. 1.

In the drawings, a catheter introducer is shown as comprising a sheath 10, a hub 12 and a strain relief fitting 14. The hub 12 includes a barbed stem 16 which receives the proximal end of the sheath 10. The two may be adhesively bonded together. The assembly is secured by means of the strain relief fitting 14 which snaps over the barbed stem 16 and prevents kinking of the sheath 10 in the area of stress concentration. The hub 12 also includes a side port 17 which is bonded to a tube 19 for feeding fluid into the sheath 10 or taking blood samples and the like.

The proximal end of body 12 is closed by an elastomeric gasket 18 and cap 20 which can be snap fit over the proximal end of hub 12 to retain the gasket 18 in place. Gasket 18 includes a slit (not shown) through which a catheter may be introduced into sheath 10. A small hole 21 is used for the introduction of a guidewire, the hole forming a better seal against the smaller diameter guidewire than the slit.

In accordance with the invention, sheath 10 is a thin wall polyimide tubing manufactured by means of a dispersion coating process. In a preferred process, a polyimide polymer is dispersed in a solvent (methylpyrrolidone) and applied to a forming mandrel. The coating is permitted to cure (i.e. dry) on the mandrel and then removed and cut to size. The process results in tubing having a relatively tight tolerance in inner diameter and roundness. Such tubing has been found to be particularly beneficial for use as a catheter introducer sheath since the specified inner diameter can be smaller for a given catheter than in the case of tubing manufactured by extrusion; moreover, there is no need for a subsequent heating treatment to draw down the inner diameter of the distal tip of the introducer sheath. Thus, for a given wall thickness, the outer diameter of the sheath is reduced. Moreover, using a polyimide tubing manufactured by a dispersion coating process, the wall thickness can be reduced to 0.005 inches while maintaining adequate kink resistance during introduction of the introducer sheath into the vasculature.

Suitable thin wall polyimide tubing manufactured by a dispersion coating process is available from HV Technologies, Inc. of Trenton, Ga. in various sizes and with various inner diameters.

As shown in FIG. 2, the inner diameter B of a dispersion coated polyimide sheath 10 may be constant for its entire length. The wall thickness is equal to 0.005 inches for almost the entire length. The outer diameter A is constant for most of its length but at its distal tip it is tapered to a wall thickness of about 0.002 inches to facilitate introduction of the introducer sheath into the blood vessel.

As indicated above, the sheath is initially introduced into the patient's blood vessel with the assistance of a dilator which extends from the distal tip of the introducer sheath. Since the dilator used with the invention may be conventional, it is not illustrated in the drawings.

The table below provides the preferred values for the outer diameter A and the inner diameter B of the sheath 10 for different sized catheters as measured by French sizes.

| Catheter French Size | A | B |
|---|---|---|
| 4F | 0.067" | 0.057" |
| 5F | 0.079" | 0.069" |
| 6F | 0.092" | 0.082" |
| 7F | 0.105" | 0.095" |

We claim:

1. A catheter introducer for facilitating the introduction of a catheter into a patient's vasculature, comprising:
    a hub having a proximal end and a distal end;
    an elongated polyimide sheath connected at the distal end of the hub, having an unsupported interior surface; and
    a gasket at the proximal end of the hub for enabling a catheter to be introduced into said sheath, wherein said sheath has an outer diameter, a constant inner diameter along substantially its entire length, and a wall thickness of no greater than 0.005 inches.

2. A catheter introducer according to claim 1 wherein the wall thickness of the polyimide sheath is approximately 0.005 inches for substantially its entire length.

3. A catheter introducer according to claim 2 wherein the outer diameter of the sheath is tapered at a distal end.

* * * * *

UNITED STATES PATENT AND TRADEMARK OFFICE
CERTIFICATE OF CORRECTION

PATENT NO. : 6,033,388

DATED : March 7, 2000

INVENTORS : Norstrom *et al.*

It is certified that an error appears in the above-identified patent and that said Letters Patent is hereby corrected as shown below.

On the front page, in items [19] and [75], please delete "Nordstrom" and insert --Norstrom-- therefor.

On the front page, in item [56], please delete "Sadola" and insert --Sadula-- therefor.

In col. 1, line 51, please delete "polyethylenebutylacrylate" and insert --polyethylene block amide--.

In col. 1, line 59, please delete "cathetheter" and insert --catheter-- therefor.

Signed and Sealed this

Seventeenth Day of April, 2001

*Attest:*

NICHOLAS P. GODICI

*Attesting Officer*     *Acting Director of the United States Patent and Trademark Office*